(12) United States Patent
Horton et al.

(10) Patent No.: US 10,907,148 B2
(45) Date of Patent: Feb. 2, 2021

(54) METHOD AND KIT FOR ANALYTE DETECTION

(71) Applicant: Global Life Sciences Solutions Operations UK Ltd, Sheffield (GB)

(72) Inventors: Jeffrey Kenneth Horton, Cardiff (GB); Peter James Tatnell, Cardiff (GB)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 44 days.

(21) Appl. No.: 15/753,343

(22) PCT Filed: Aug. 18, 2016

(86) PCT No.: PCT/EP2016/069576
§ 371 (c)(1),
(2) Date: Feb. 19, 2018

(87) PCT Pub. No.: WO2017/036808
PCT Pub. Date: Mar. 9, 2017

(65) Prior Publication Data
US 2018/0245068 A1 Aug. 30, 2018

(30) Foreign Application Priority Data
Aug. 28, 2015 (GB) .................................. 1515355.4

(51) Int. Cl.
*C12N 15/115* (2010.01)
*C12N 15/10* (2006.01)
*C12Q 1/6834* (2018.01)

(52) U.S. Cl.
CPC ........ *C12N 15/1048* (2013.01); *C12N 15/115* (2013.01); *C12Q 1/6834* (2013.01); *C12N 2310/16* (2013.01); *C12N 2320/13* (2013.01); *C12N 2330/31* (2013.01)

(58) Field of Classification Search
CPC .............. C12N 15/1048; C12N 15/115; C12N 2310/16; C12N 2320/13; C12N 2330/31; C12Q 1/6834
See application file for complete search history.

(56) References Cited

U.S. PATENT DOCUMENTS

2012/0149008 A1 6/2012 Choi et al.
2013/0330777 A1* 12/2013 Zhang ................. C12Q 1/6846
435/91.2
2014/0113294 A1* 4/2014 Horton ................. C12Q 1/686
435/6.12
2014/0154667 A1 6/2014 Lamerton et al.
2014/0303030 A1 10/2014 Reinemann et al.

FOREIGN PATENT DOCUMENTS

| WO | 2014/072354 A1 | 5/2014 |
| WO | 2014/099121 A1 | 6/2014 |
| WO | 2014/143714 A2 | 9/2014 |
| WO | 2015/090879 A1 | 6/2015 |

OTHER PUBLICATIONS

Pinto et al. (Molecular Biosystems (2009) vol. 5, pp. 548-553). (Year: 2009).*
PCT International Search Report and Written Opinion for PCT Application No. PCT/EP2016/06576 dated Nov. 9, 2016 (12 pages).
GB Search Report for GB Application No. 1515355.4 dated Jun. 23, 2016 (4 pages).
Layzer et al., "Simultaneous Generation of Aptamers to Multiple Gamma-Carboxyglutamic Acid Proteins from a Focused Aptamer Library Using DeSELEX and Convergent Selection," Oligonucleotides, 2007, 17:1-11.
Li et al., "Amplified Electrochemical Aptasensor Taking AuNPs Based Sandwich Sensing Platform as a Model," Biosensors and Bioelectronics, 2008, 23:965-970.
Li et al., "Detection of Protein Biomarkers Using RNA Aptamer Microarrays and Enzymaticalkly Amplified Surface Plasmon Resonance Imaging," Anal. Chem., 2007, 79:1082-1088.
Su et al., "Adsorption and Covalent Coupling of ATP-Binding DNA Aptamers onto Cellulose," Langmuir, 2007, 23:1300-1302.
Tao et al., "Evaluation of a Solid Matrix for Collection and Ambient Storage of RNA from Whole Blood," BMC Clinical Pathology, 2014; 14(22):1-9.
Tsukakoshi et al., "Selection of DNA Aptamers that Recognize α-Synuclein Oligomers Using a Competitive Screening Method," Anal. Chem., 2012, 84:5542-5547.
Yoshida et al., "Quantitative and Sensitive Protein Detection Strategies Based on Aptamers," Proteomics Clin. Appl., 2012,6:574-580.
Zhao et al., "Rolling Circle Amplification: Applications in Nanotechnology and Biodetection with Functional Nucleic Acids," Angew. Chem. Int. Ed., 2008, 47:6330-6337.

* cited by examiner

*Primary Examiner* — J. E. Angell
(74) *Attorney, Agent, or Firm* — Eversheds Sutherland (US) LLP

(57) ABSTRACT

The present invention relates to a method and kit for analyte detection. More precisely the invention relates to a method of detecting an analyte, comprising storing short single stranded nucleic acids (10-100 nt), such as aptamers and micro RNA, on a solid support at ambient temperature; and subsequent amplification of said nucleic acids for detection of analyte(s).

9 Claims, 3 Drawing Sheets

METHOD AND KIT FOR ANALYTE DETECTION

CROSS REFERENCE TO RELATED APPLICATIONS

This application claims the priority benefit of PCT/EP2016/069576 filed on Aug. 18, 2016 which claims priority benefit of Great Britain Application No. 1515355.4 filed Aug. 28, 2015. The entire contents of which are hereby incorporated by reference herein.

FIELD OF THE INVENTION

The present invention relates to a method and kit for analyte detection. More precisely the invention relates to a method of detecting an analyte, comprising storing short single stranded nucleic acids (10-100 nt), such as aptamers and micro RNA, on a solid support at ambient temperature; and subsequent amplification of said nucleic acids for detection of an analyte.

BACKGROUND OF THE INVENTION

Biological sample storage and preservation is desired as the preserved sample can be used for various applications, such as analyte detection, sensing, forensic and diagnostic applications, genome sequencing, whole-genome amplification, and the like.

Some of the currently used devices for preservation of samples on paper substrates are available. Porous or non-porous substrates are commonly used for preservation of biological samples, such as paper cards or membranes. Examples of paper cards or membranes include chemically treated FTA® and FTA® Elute papers (GE Healthcare) for preservation of nucleic acid samples, and the FTA® DMPK cards and 903® cards (GE Healthcare) for preservation of blood samples. The substrates employed a method of absorption and drying of a wet biological sample, such as blood, buccal swabs or macerated tissue disposed on the substrate.

Rolling circle amplification (RCA) is an isothermal DNA amplification process mediated by DNA polymerases in which ssDNA is synthesised via circular templates. It is used for signal amplification in ultra-sensitive DNA detection assays. RCA has been adapted to amplify sequences that encode DNA aptamers and DNA/RNAzymes. [Rolling circle amplification: Applications in Nanotechnology and Bio-detection with functional nucleic acids. Zhao W et al 2008. Angew Chem Int Ed 47, 6330-6337.]

Aptamers are single stranded nucleic acid (ssDNA or ssRNA) molecules that are able to bind a range of different chemical and biochemical moieties such proteins, small molecular weight compounds, metabolites, chemical compounds etc. This binding event is aptamer and analyte-specific and can be engineered to be highly specific, with high affinity. Therefore aptamers share many comparable properties with monoclonal antibodies and are now being considered viable alternatives in many processes in which antibodies have been traditionally used.

Aptamers can be designed to bind different epitopes on the same target molecule, facilitating the production of a detection system comparable to the immunologically based ELISA. Detection systems have been generated incorporating flurophores into amplified aptamers or by generating aptamer-based DNAzymes (catalytic enzymes that convert reporter dyes) and ribozymes. The use of aptamers that bind different analytes and non-overlapping detection reagents will support multiplex assays designed to detect different agents in the same reaction vessel.

Systematic evolution of ligands by exponential enrichment (SELEX) is a combinatorial chemistry technique in molecular biology for producing oligonucleotides of either single-stranded DNA or RNA that specifically bind to a target ligand or ligands. The process begins with the synthesis of a very large oligonucleotide library consisting of randomly generated sequences of fixed length flanked by constant 5' and 3' ends that serve as primers. For a randomly generated region of length n, the number of possible sequences in the library is $4^n$ (n positions with four possibilities (A, T, C, G) at each position). The sequences in the library are exposed to the target ligand—which may be a protein or a small organic compound—and those that do not bind the target are removed, usually by affinity chromatography. The bound sequences are eluted and enriched by nucleic acid amplification to prepare for subsequent rounds of selection in which the stringency of the elution conditions is increased to identify the tightest-binding sequences.

However, there are stability problems with the use of short nucleic acids like specific aptamers and libraries of aptamers and it would be desirable to have a solution which allows long term stabilization of aptamers at ambient temperature prior to and during the SELEX enrichment, selection and detection process.

SUMMARY OF THE INVENTION

The present invention solves the stability problems of aptamers by providing use of solid supports as a long-term ambient temperature storage media for short nucleic acid sequences between 10-100 nucleotides (nt) in length encoding ssDNA and ssRNA aptamers.

The support may be a matrix, a paper, a fibrous web, a membrane, or a foam. The support may comprise fibres, e.g. cellulose or glass fibres, and optionally other components, such as e.g. particulate fillers, wet strength additives or dry strength additives or retention agents. The support is preferably a solid paper support, such as FTA® or RSM (RNA Stabilization matrix; Tao et al 2014; Evaluation of a solid matrix for collection and ambient temperature storage of RNA from whole blood. BMC Clinical Pathology, 14, 22; pp 1-9).

In a first aspect the invention provides a method of detecting one or more analyte(s), comprising storing low molecular weight single stranded nucleic acids (10-100 nt), such as aptamers and micro RNA, on a solid support; and amplifying said nucleic acids. The nucleic acids are stored on the solid support by depositing a solution comprising the nucleic acids on the solid support and drying the solution on the support.

The present inventors have discovered that the low molecular weight single stranded nucleic acids, such as 10-100 nt may be stabilized on the solid support at ambient temperature for a prolonged time between storage and subsequent amplification reaction. The low molecular weight nucleic acids are preferably specific ssDNA or ssRNA aptamers or a library of aptamers and the method comprises a step of binding analyte(s) with said amplified aptamers for analyte detection or aptamer selection prior to analyte detection.

The solid support comprises: cellulose based paper, woven or non-woven fibrous materials, including man made, or naturally occurring polymer fibres, mineral fibre based materials such as glass fibre materials, or surface treated solid materials for example, chemically or mechanically treated materials, including laser etched surfaces, all provided with a surface roughness of sufficient roughness to hold principally DNA RNA and protein molecules, or a gel, such as alginate, all optionally chemically treated with a stabilising reagent or reagent mix. Preferred supports are cellulose-based, polymers, fibres and chemically coated papers such as RSM, FTA™, FTA Elute™ uncoated papers such as 903™ 31-ETF cellulose papers. The reagent or reagent mix comprises: a weak base, an antioxidant and a chelating agent, and optionally an anionic surfactant, or comprises: a chaotropic substance such as a chaotropic salt. Examples are SDS, EDTA, antioxidant (Uric acids, TCEP (Tris(2-carboxyethyl)phosphate), THQ (toluhydroquinone), guanidinium HCl, guanidinium thiocyanate.

In one embodiment of the method the solid support, or a portion thereof, such as a punch, provided with stored aptamers is excised and put in a reaction well or tube which already is or will be provided with amplification reagents. Optionally the excised solid support can be washed and optionally the aptamers are extracted from the solid support and added as a solution to the subsequent amplification step In a further embodiment said portion or punch with stored aptamers is put in a reaction well of a reaction plate and said well is provided with amplification reagents, and wherein the stored aptamers are amplified in the reaction well. Optionally the excised solid support is washed.

All the wells of the reaction plate are preferably provided with amplification reagents in a freeze dried format as exemplified by the GE Healthcare ready to go format (RTG) and all wells may be provided with a punch and the punches may be provided with the same or different aptamers.

In a further embodiment the wells of the reaction plate are coated with primary aptamers and the aptamers amplified from the punches act as secondary aptamers in a detection reaction of an analyte. In this reaction the primary aptamers are directed against a first epotipe or binding site on the analyte and the secondary aptamers against a second epitope on the analyte. In this embodiment specific aptamers are covalently attached to specific regions of a reaction vessel such as a 96-well plate. These primary aptamers are tethered to the solid support using traditional tethering reagents e.g. N-succimidyl propionate. Biological samples are applied followed by the addition of punch with stabilized aptamers (generated as described above) to the reaction vessel including amplification reagents for amplification of the secondary aptamers. These tethered and soluble aptamers are designed to bind different epitopes of the same target molecule, thereby facilitating a solid support system based upon aptamers akin to an ELISA-type reaction. The appropriate nucleic acid amplification reagents and detection systems are preferably incorporated in a RTG (ready to go-format.

The amplifying method used in the invention is preferably RCA, Rolling Circle Amplification. This is the preferred amplification reaction although other amplification reactions also may be used, such as PCR. PCR, isothermal amplification e.g. helicase dependent amplification, RNA amplification; NASBA (Nucleic acid sequence-based amplification—a one-step isothermal process for amplifying RNA), RNA-dependent RNA polymerase. Optionally, the amplification may be performed in the presence of cyclodextrin. Cyclodextrin sequestrates free SDS from solutions. SDS is a protein denaturant and if present will inhibit downstream enzyme-based applications e.g. PCR. Cyclodextrin binds the SDS and thus effectively removes it.

For detection the amplified aptamers are provided with reporter molecules, such as fluorophores. Any colorimetric detection system demonstrating compatibility with aptamers and analyte binding assays may be used. These range from incorporating flurophores into amplified aptamers to generating aptamer-based DNAzymes that are able to mimic catalytic enzymes that act upon reporter dyes thereby generating coloured signals. The method and kit of the invention may also be used in a microfluidics or biosensor format using impedance measurement.

In a second aspect, the invention relates to a kit comprising aptamers stored on solid paper support and a reaction plate provided with reaction wells comprising amplification reagents. The solid support with aptamers may be provided as a paper sheet or punches/pieces thereof ready for insertion into the reaction plate. Alternatively the punches may already be inserted in the reaction wells. Preferably, the reaction wells are provided with ready to go (RTG) amplification reagents.

In the kit, the wells of the reaction plate may be coated with primary aptamers. In this case the aptamers on the solid support will act as secondary aptamers in a reaction for detection of an analyte in a similar way as in an ELISA-reaction.

In a preferred embodiment of the invention the stabilized aptamers are directly amplified to generate large amounts of aptamers from a single punch of the storage media added directly to an amplification reaction. The combination of stabilized aptamers with RCA or other amplification reaction generates binding assays for the detection of a range of molecular targets e.g. proteins, metabolites in proteomics, diagnosis & bio-sensing.

In a third aspect the invention relates to use of solid paper supports to store low molecular weight nucleic acids (10-100 nt), preferably specific aptamers or libraries of aptamers. This use enables convenient storage of aptamers at ambient temperature for prolonged time. The solid paper supports are of the same kind as described above and are particularly suitable for transportation compared to aptamers in solution.

The aptamers applied to solid supports are used to select for i) specific aptamers with either higher binding affinities to previously screened for aptamers or ii) selecting new aptamers against specific analytes. SELEX is used to produce and select aptamers against target molecules. This involves multiple rounds of screening followed by amplification. Solid supports provide a matrix that allows convenient ambient temperature storage of nucleic acid molecules prior to the next round of amplification and selection. Preferably the aptamers are RNA aptamers and the solid support preferably is RSM.

The method and kit provided by the present invention has significant advantages over the process currently used in that the solid-support i) stores the aptamer at ambient temperature whereas antibodies or other binding agents require specialised cold storage and ii) in-combination with the relevant/appropriate amplification RTG (ready-to-go) reagents it can be used to generate significant amounts of the specific aptamer. As described in the Examples, data has been generated that demonstrates that applying punches containing biological samples to reaction mixture does not inhibit nucleic amplification, immunological protein-binding or detection events.

DETAILED DESCRIPTION OF THE INVENTION

Figure 1:
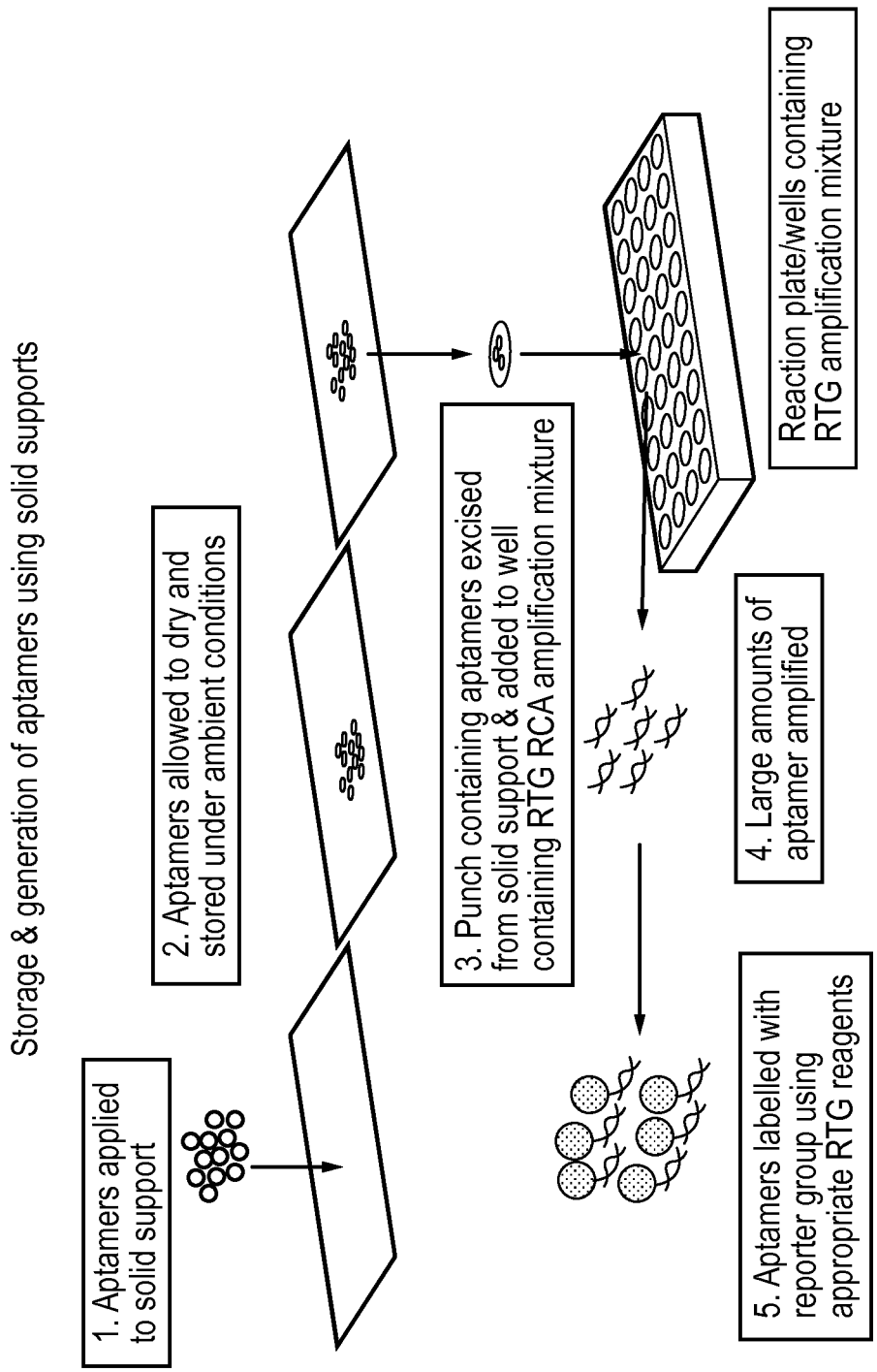
FIG. 1 is a schematic view of the process from of storage of specific aptamers on paper support and punching paper circles into reaction wells to amplification of specific analytes reacting with the stored aptamers.

Example 1—Storage and Recovery of Small Molecular RNA from Chemically-Coated Cellulose-Based Solid Supports This example shows that biological samples spotted onto chemically-coated cellulose-based solid support matrices can be stored at ambient conditions prior to the isolation and purification of small single-stranded molecular weight RNA molecules (~20 nt in length) as exemplified by RNA aptamers and micro RNAs.

Immediately after the collection of whole blood in EDTA by venous puncture, 40 μl aliquots were spotted onto cellulose-based solid supports and allowed to dry. Total RNA was subsequently isolated from the solid supports using the Illustra RNAspin mini RNA Isolation kit (GE Healthcare) and the Illustra TriplePrep kit (GE Healthcare). The presence of the small molecular weight micro RNAs were detected and quantified using a two-step quantitative reverse-transcriptase PCR (QRTPCR) with micro RNA specific primers and probes.

illustra Ready-To-Go products (GE Healthcare) are pre-formulated and pre-dispensed, freeze-dried reagent mix in a format for robust and reproducible performance in standard laboratory techniques such as nucleic acid amplifications e.g. PCR, RT-PCR etc. Ready-to Go formats can also be formulated to stabilise proteins, enzymes, antibodies etc. The Illustra PuReTaq Ready-To-Go PCR Beads are pre-mixed, predispensed, single-dose reactions optimized for performing standard PCR amplifications. The use of recombinant PuReTaq DNA polymerase and other high-purity reagents ensures reliable and robust performance in both end point and real-time fluorescence-based PCR amplifications. The puReTaq Ready-To-Go PCR reagents are pre-formulated to ensure greater reproducibility between reactions, minimize pipetting steps, and reduce the potential for pipetting errors and contamination. The only additional reagents required are water, primers, and template DNA. The Ready-To-Go products are stable at room temperature and designed for performing single-tube one-step reverse transcription-PCR. Each room-temperature-stable product contains M-MuLV Reverse Transcriptase, RNase Inhibitor, buffer, nucleotides, and Taq DNA Polymerase. The only additional reagents required are water, template RNA, and primers. The reagents are optimized for full-length cDNA synthesis to >7.5 kb and optimal sensitivity from PCR.

Use of Solid Support Matrices with Illustra RNAspin Mini RNA Isolation Kit

1. After collection in EDTA, blood was applied to paper-based solid support matrices in 40 μl aliquots and dried for a minimum of 3 hr at room temperature.

2. Using a sterile Harris 5 mm disposable micro punch (GE Healthcare) and a punch mat, discs were removed from the centre of dried sample spots and placed in clean RNase-free 1.5 ml micro-centrifuge tube.

3. Buffer RA1 (350 μl, from the Illustra kit) was added to each tube, followed by 3.5 μl mercaptoethanol; each disc was then homogenized using a 20 gauge needle.

4. Homogenates were transferred to the filter columns supplied with the Illustra kit and protocol supplied with the Illustra RNAspin mini RNA Isolation Kit was followed. RNA elution was performed in 50 μl RNase free water.

Use of Solid Support Matrices with Illustra TriplePrep Kit

1. After collection in EDTA, blood was applied to cellulose-based solid support matrices (Support 1 is FTA® and Support 2 is FTA Elute®) in 40 μl aliquots and dried for a minimum of 3 hr at room temperature 2. Using a Harris 5 mm disposable micro punch and a punch mat, discs were removed from the centre of dried sample spots and placed in clean RNase-free 1.5 ml micro-centrifuge tube.

3. Buffer RA1 (350 μl, from the Illustra TriplePrep kit) was added to each tube, followed by 3.5 μl β-mercaptoethanol; each disc was homogenized using a 20 gauge needle.

4. Homogenates were transferred into DNA mini columns supplied with the TriplePrep kit. These were then centrifuged at 11,000×g for 1 min. DNA columns were discarded and the protocol described in the Illustra TriplePrep Kit was followed. RNA elution was performed in 50 μl RNase free water.

Total RNA Isolation from Whole Blood Using Trizol

1. TRIZOL® Reagent (1 ml) was added to 500 μl whole blood in a 1.5 ml microfuge tube and briefly vortexed.

2. Homogenized samples were incubated for 5 min at 30° C.

3. Chloroform (0.2 ml per 1 ml of Trizol) was added. Sample tubes were securely closed and shaken vigorously by hand for 15 seconds before incubation at 30° C. for 2 to 3 min.

4. Samples were centrifuged at 12,000×g for 15 min at 8° C. Note: following centrifugation, the mixture separates into a lower red, phenol-chloroform phase, an interphase, and a colourless RNA-containing upper aqueous phase.

5. The aqueous phase was transferred to a fresh 1.5 ml tube. RNA was precipitated from the aqueous phase by mixing with 0.5 ml isopropyl alcohol per 1 ml of Trizol used for the initial homogenization, followed by incubation of samples at 30° C. for 10 min. Precipitated RNA was pelleted by centrifugation at 12,000×g for 10 min at 8° C.

6. Supernatants were removed and RNA pellets washed once by vortex with 1 ml 75% ethanol and then centrifuging at 7,500×g for 5 min at 2 to 8° C.

7. Pellets were air dried and then re-suspended in 50 μl RNase free water. For comparison against blood stored on cellulose-based solid support matrices, aliquots of blood for Trizol extraction were stored at 4° C., and then rocked for 1 hr at room temperature prior to the day 1 or day 2 isolations.

miRNA analysis—Samples eluted using the Illustra RNAspin kit, TriplePrep kit, or trizol extractions were analysed for total RNA content before miRNA analysis. Quantification of eluted total RNA was performed by QRTPCR using a 7900HT thermal cycler (Applied Biosystems) in order that the amount of template RNA used in subsequent micro RNA quantification reactions could be normalized. Reactions were set up using the TagMan EZ-RT PCR Kit (Applied Bio-systems) with GAPDH control reagents (Applied Biosystems). Standard curves for RNA quantification were prepared using a five point serial dilution from 5 ng/μl to 0.5 pg/μl of control RNA supplied with the kit. Primers included with the TagMan EZ-RT PCR Kit for RNA analysis were designed across introns to ensure that only cDNA was amplifiable.

Presence of microRNA in eluates was determined by QRTPCR using a 7900HT thermal cycler. Reactions were set up using a two-step TagMan protocol (Applied Biosystems). The TagMan RT micro RNA reagent kit (#4366596) was used to transcribe cDNA from 5 μl total RNA with primers specific for the micro-RNAs miR-223, miR-191 and miR-26a using the following Applied Biosystems kits hsa-miR-223 (Cat no 4395209), hsa-miR-191 (cat no. 4395410) and hsa-miR-26a-1 (Cat no 4395166) respectively prior to running the TagMan QPCR. Protocols were followed as described in the Applied Bio-systems manual. The only deviation from this was the use of a 96 well block.

Results—Initial experiments focused on whether micro RNAs could be isolated from cellulose-based solid supports using the Illustra RNAspin and TriplePrep kits. In addition, experiments also evaluated micro RNA stability on the matrices using blood that had been stored on the matrices for 24 and 48 hr. As a control, total RNA was isolated from whole blood by Trizol extraction.

Figure 2:
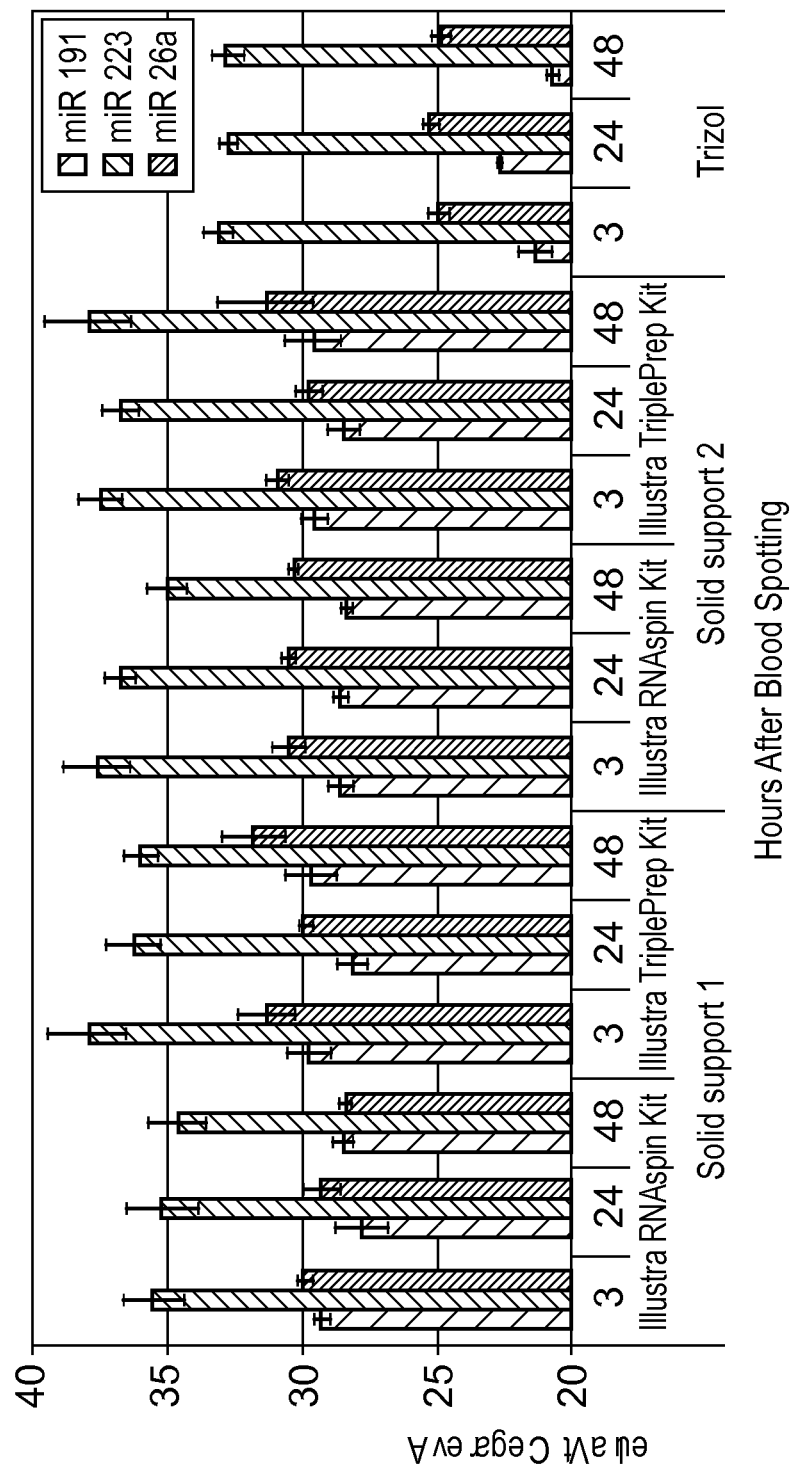
FIG. 2 shows the results of micro RNA expression detection using QRTPCR. For each bar, n=4; error bars represent standard deviations.

Results (FIG. 2) shows that small molecular weight RNA molecules such as micro RNA can be successfully stored and isolated from chemically coated cellulose based solid supports using both the GE Healthcare Illustra RNAspin and the TriplePrep kits.

The amounts of micro RNA detected derived from the solid supports were comparable over the time frame tested i.e. 3, 24 and 48 hr, indicating that micro RNA is stable on both solid supports tested. Quantification of total RNA showed that yields eluted from both matrices using TriplePrep kit were approximately 1/10th of those obtained using the RNAspin kit. This is not surprising however; as while the former is designed to isolate DNA, RNA and protein, the latter is RNA-specific.

It should be noted that the minimum amount of total RNA suggested for use with the Applied Bio-systems microRNA TagMan assays is 1 ng/5 μl total RNA used in each reaction. In these experiments we were able to quantitate microRNAs in 16 pg/5 μl total RNA per reactions.

Without micro RNA standards, it was not possible to absolutely quantify individual micro RNA tested. However Ct values obtained by QRTPCR provide a valuable indication of relative expression levels. Note that lower Ct values indicate greater expression and higher Ct values indicate lesser expression levels. Ratios between the expression levels of individual micro RNA were not altered by either the solid support used, the extraction kit or storage time.

In order to understand if the micro RNA fraction present in pre-purified total RNA is stable on the cellulose-based solid supports, total RNA from whole blood was isolated using the Trizol extraction process. Isolated total RNA samples were then applied to solid supports and allowed to dry for 3 hrs prior to extraction using the Illustra RNAspin kit. Total RNA extracted from the blood using the Trizol reagent was used as a control. Subsequent analyses were performed as described above. Total RNA extracted from the solid supports and directly from the Trizol extracted blood was quantified using GAPDH QRTPCR and 0.45 ng total RNA was used in the micro RNA QPCR.

Figure 3:
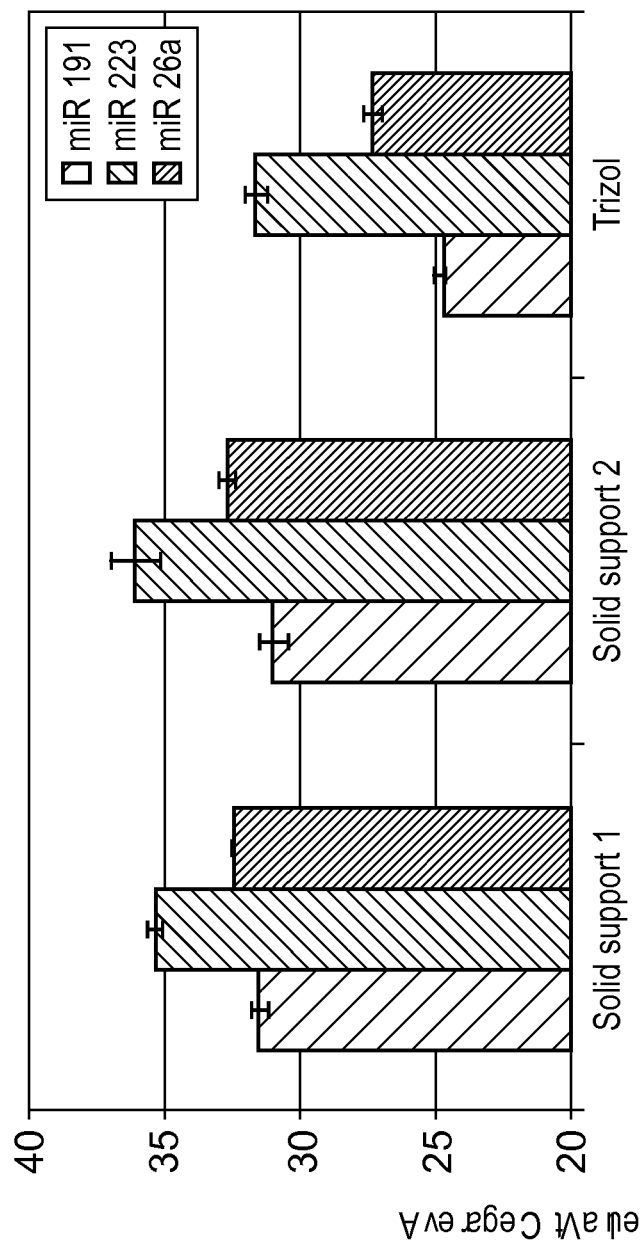
FIG. 3 shows Ct values as determined by QRTPCR for each miRNA analysed. Total RNA was extracted from blood and applied to each solid support and dried for 3 hr before extraction using an Illustra RNAspin kit. Micro RNA expression was detected using 0.45 ng total RNA per reverse transcription reaction. For each bar, n=4; error bars represent standard deviations.

The presence of all three individual micro RNAs was detected in total RNA applied to the solid supports (FIG. 3). Comparison of micro RNA relative yields as estimated from Ct values from samples applied to the solid supports with those from whole blood using Trizol (FIG. 3) indicates that some micro RNA may be lost during the drying or processing of the cellulose-based solid supports. This is evident because although total RNA quantity was normalized before QRTPCR, the lower Ct values obtained for Trizol samples indicate that samples extracted using this method contained greater amounts of micro RNA.

In conclusion, the chemically coated solid supports facilitate the storage, purification and detection of small molecular weight RNA molecules as exemplified by the three microRNAs used in this example. Using the system described, detection limits for individual microRNAs were as low as 16 pg per reaction. This experiment clearly demonstrates that small molecular weight RNA molecules can be stored on chemically-coated cellulose-based solid supports for prolonged time periods.

Example 2—Extraction and Analysis of mRNA Molecules from Biological Samples Applied to the Chemically-Coated RSM Solid Support Rat blood collection and dried blood spot extraction—Male Sprague-Dawley rats (180-250 g) were purchased from Charles River Laboratories. Whole blood was collected via pipette directly from a 26 gauge catheter placed in the tail vein of anaesthetized rats. Fifty microliter aliquots were transferred without anticoagulant and spotted onto chemically-treated and untreated filter papers. Blood spots were dried and maintained at ambient lab temperature for 11 days in a desiccator cabinet (~20% relative humidity). Two sample discs were punched from each dried blood spot using a 7 mm Harris Uni-Core punch (Fisher Scientific) treated with 15 μl PK solution (4 mg/ml proteinase K+0.5% SDS) per punch. Sample discs were transferred into a 1.5 ml micro-centrifuge tube containing 350 μl of extraction solution (RLT buffer with 1% β-mercaptoethanol, Qiagen) and incubated for 20 min at 40° C. on a Thermo-mixer (Eppendorf) at 700 rpm. After incubation, RNA was purified from 350 μl of eluate using QIAamp RNA Blood Mini kit (Qiagen) and eluted in 40 μl of nuclease-free water.

Human blood collection and application onto RSM paper—Venous blood samples were collected via phlebotomy into EDTA or heparin coated blood tubes (Fisher Scientific). Immediately after blood drawing and mixing, 50 μl of blood was pipetted from the blood tubes and applied onto one piece of RSM paper by dispensing in a circular motion within the spotted circle. The samples were allowed to dry at room temperature for ~2 hours and then placed back into the original Mylar pouch with fresh desiccant and stored at three different conditions: overnight (18 hours) at room temperature (~25° C.), 6 days at room temperature or overnight (18 hours) at 37° C.

RNA extraction from RSM paper—Four to five 6 mm sample discs were prepared from each dried blood spot by using a 6 mm Harris Uni-Core punch (Fisher Scientific). The sample discs were placed on parafilm and 15 μl PK solutions (4 mg/ml proteinase K+0.5% SDS) was added onto each disc and incubated at room temperature for 15 minutes. Discs from 2 blood spots were placed into 1.5 ml micro-centrifuge tubes containing 800 μl of extraction solution (RLT buffer with 1% β-mercaptoethanol, Qiagen) and incubated for 30 min at 37° C. on a Thermo-mixer (Eppendorf) at 600 rpm. After incubation, 700 μl of eluate was transferred to a new micro-centrifuge tube and mixed with 400 μl of isopropanol and 10 μl SPRI beads from the Agencourt RNAdvance Blood kit (Beckman Coulter Genomics). RNA was then extracted following the manufacturer's instruction;

genomic DNA removal was performed using the Ambion DNase I kit (Ambion) at 37° C. for 10 min. PAXgene RNA blood collection and RNA extraction.

Human whole blood samples were collected in PAXgene® RNA Blood Tubes according to the manufacturer's instructions (PreAnalytix). RNA was isolated by means of a magnetic bead based approach using a modified version of the Agencourt RNAdvance Blood kit (Beckman Coulter Genomics) and the Hamilton STAR automated liquid handler (Hamilton). Extraction was performed in 96-well plates containing 400 µl of whole blood per well; genomic DNA removal was performed using the Ambion DNase I kit (Ambion) at 37° C. for 10 min.

Internal PAX pool blood control—Approximately 2.5 mL of blood was collected in PAXgene® RNA Blood Vacutainer Tubes from consented donors (Western IRB Protocol #20090362). The blood/PAXgene reagent mixture from donor tubes were pooled together. After pooling and mixing, each pool was distributed into 1.5 ml aliquots and stored at −20° C.

RNA analysis—Purified RNA was quantified by absorbance at 260 nm using the NanoDrop 8000 (Thermo Scientific). RNA integrity was assessed by Agilent 2100 Bioanalyzer using the Eukaryote total RNA 6000 Pico Assay kit according to the manufacturer's instructions (Agilent Technologies, Palo Alto, Calif.). The RNA integrity numbers (RIN) were calculated using the Agilent 2100 Expert Software (RIN=1; lowest RNA quality to RIN=10; highest RNA quality).

Reverse transcription—RNA was reverse-transcribed to cDNA using the High Capacity Reverse Transcription Kit (Life Technologies). The RNA extracted from PAXgene tubes was adjusted to 6 ng/µl and cDNA samples diluted to a RNA equivalent of 1 ng/µl for downstream processing. All available RNA extracted from RSM paper (estimated ~200 ng) was used in cDNA reaction without mass normalization.

RT-qPCR reactions were performed by addition of 2 µl of cDNA sample onto the GES plates. All RT-qPCR reactions were run using the Light Cycler 480 II (Roche) using the following cycling condition: 50° C. 2 minutes, 95° C. 10 minutes and 45 cycles of 95° C. 15 seconds and 60° C. 1 minute. Individual Crossing point (Cp) values were calculated using LC480 II software (Roche). Genomic DNA contamination was assessed by comparing expression values for splice-junction spanning and intergenic TFCP2 assays.

Results—The baseline arm of this study utilized 25 healthy subjects and consisted of whole blood samples spotted on RSM and 31-ETF paper or collected in PAXgene tubes and stored for 18 hours at room temperature (baseline condition, RT; ~25° C.). RIN scores for the RNA obtained from the PAXgene tubes were slightly higher than those obtained from RSM (mean RIN±95% CI: 7.98±0.54 vs. 6.92±0.24 respectively, p<0.001; mean yields were higher from the PAXgene tubes (6.58 ng/µl vs. 4.79 ng/µl whole blood, respectively, p<0.001) RNA isolated from untreated 31-ETF paper showed significant degradation (2.87±0.11)

RT-qPCR—To evaluate the RNA isolated under the various conditions with a functional test, 23 genes used in a clinically validated, gene expression-based diagnostic test for obstructive coronary artery disease were assayed by RT-qPCR. Overall, only slight changes in gene expression levels were observed from RSM paper stored at 37° C. or 6 days compared to the baseline arm, with a median delta Crossing point (Cp) of 0.15 observed for both comparisons. Fifteen of the 23 genes tested showed no significant difference in expression levels (Cp values) between the 3 arms. Two genes (CD3D, TLR4) showed a significant shift in Cp values in the 37° C. arm whereas 7 genes (CD3D, IL18RAP, KLRC4, NCF4, RPL28, TNFAIP6, TNFRSF10C) showed significant shifts in the 6-day arm, with only CD3D affected significantly in both arms. In comparison, the median delta Cp between the baseline arm and 37° C. was slightly larger for PAXgene samples relative to RSM (0.53 vs. 0.15 Cp respectively; and noticeably larger for PAXgene when compared to the 6-day arm (1.97 vs. 0.15 Cp;). Thus, for the 23 genes analyzed, mean gene expression from RSM paper was less sensitive to elevated temperature or prolonged storage compared to PAXgene-stabilized RNA.

The invention claimed is:

1. A method comprising:
    storing dried low molecular weight single stranded nucleic acids (10-100 nt) applied on a solid support, wherein the nucleic acids are DNA or RNA aptamers;
    combining i) the solid support or ii) a portion thereof excised as a punch provided with the stored DNA or RNA aptamers in a reaction well or tube with amplification reagents;
    amplifying said DNA or RNA aptamers from the solid support to form secondary aptamers; and
    detecting the one or more analytes(s) by binding analyte(s) with said amplified secondary aptamers and primary aptamers,
    wherein the wells of the reaction well or tube are coated with the primary aptamers, and
    wherein the primary aptamers and secondary aptamers are directed to first and second epitopes on the same analyte.

2. The method according to claim 1, wherein said solid support comprises: cellulose based paper, woven or non-woven fibrous materials, man made, or naturally occurring polymer fibres, mineral fibre based materials, glass fibre materials, or surface treated solid materials, chemically or mechanically treated materials, laser etched surfaces, all provided with a surface roughness of sufficient to hold DNA, RNA and protein molecules, all chemically treated with a stabilising reagent or reagent mix.

3. The method according to claim 2, wherein said reagent or reagent mix comprises: a weak base, an antioxidant, a chelating agent, and an anionic surfactant, or comprises: a chaotropic substance.

4. The method according to claim 1, further comprising extracting the aptamers from the solid support and adding the extracted aptamers in a solution to the subsequent amplification step.

5. The method according to claim 1, wherein said punch with stored aptamers is put in a reaction well of a reaction plate and said well is provided with amplification reagents, and wherein the stored aptamers are amplified in the reaction well.

6. The method according to claim 1, wherein the amplification reagents are present in the reaction wells as freeze dried material.

7. The method according to claim 1, wherein the solid support comprises cellulose based paper and amplifying of aptamers is made by rolling circle amplification.

8. The method according to claim 1, wherein the amplified aptamers are provided with reporter molecules, fluorophores, catalytic aptamers, ribozymes or DNAzymes.

9. The method according to claim 1, wherein the storing of the dried low molecular weight single stranded nucleic acids (10-100 nt) applied on the solid support is at ambient temperature.

* * * * *